(12) United States Patent
Yanai et al.

(10) Patent No.: US 6,620,411 B1
(45) Date of Patent: Sep. 16, 2003

(54) METHOD FOR INHIBITING BRAIN TUMOR OR COLON CARCINOMA

(75) Inventors: Akira Yanai, Yokosuka (JP); Saburo Sone, Yokohama (JP); Akemi Kajita, Fujisawa (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/806,684

(22) PCT Filed: Aug. 6, 1999

(86) PCT No.: PCT/JP99/04281

§ 371 (c)(1),
(2), (4) Date: Jun. 6, 2001

(51) Int. Cl.⁷ .................. A61K 38/21; A61K 38/00; C07K 14/00; C07K 17/00
(52) U.S. Cl. .................. 424/85.6; 424/85.4; 514/2; 514/12; 530/350; 530/351
(58) Field of Search ............... 424/85.4, 85.6; 514/2, 12; 530/350, 351

(56) References Cited

PUBLICATIONS

Cook et al. Human brain tumor–derived cell lines: Growth rate reduced by human fibroblast interferon. (1983), Science, vol. 219, pp. 881–883.*

Wong et al. Growth–inhibitory activity of interferon–beta against human colorectal carcinoma cell lines. (1989), Int. J. Cancer, vol. 43, pp. 526–530.*

Niijima et al. Intravesical treatment of bladder cancer with recombinant human interferon–beta. (1989), Cancer Immunology, vol. 30, pp. 81–85.*

Rotolo et al. Beta–Interferon treatment of cervical intraepithelial neoplasia: a multiceter clinical trial (1995), Intervirology, vol. 38 (6), pp. 325–331.*

Yung et al. Intravenous recombinant interferon beta in patients with recurrent malignant gliomas: aphase I/II study. (1991), J. Clin. Oncol: 11:1945–1949.*

* cited by examiner

Primary Examiner—Lorraine Spector
Assistant Examiner—Jegatheesan Seharaseyon
(74) Attorney, Agent, or Firm—Kubovcik & Kubovcik

(57) ABSTRACT

A method for inhibiting cell growth is provided. The method includes the step of systemically administering a pharmaceutical preparation containing an interferon as an active ingredient two or more times a day, and is specifically useful for cancer treatment.

3 Claims, 2 Drawing Sheets

METHOD FOR INHIBITING BRAIN TUMOR OR COLON CARCINOMA

TECHNICAL FIELD

The present invention is related to a method for inhibiting cell growth intended for especially tumor cells, which is useful clinically and experimentally.

BACKGROUND ART

According to the vital statistics of Japan in 1994, the deceased number by cancer increases 7878 people from the previous year and is 244000 people. In this way, the deceased number by cancer has held the top spot since 1981 and occupies 28% of the total number of deaths. When the subjects are limited to the 50 from the 40 years old, the deceased number by cancer amounted to about one third of the total deceased number, and the number of cancer patients was 1327000 in the year of 1993. Recently, a variety of anticancer drugs and therapy have been developed, but the cancer is the big subject that still should be tackled.

The application the interferon has been tried to various cancers, in world every country heretofore. At present, the efficacy of interferon is seen in, for example, hairy cell leukemia, Kaposi sarcoma, chronic myeloid leukemia, non-Hodgkin's lymphoma, multiple myeloma, malignant melanoma, and renal cell carcinoma (Tyringt et al., "Interferon" pp. 399–308, edited by Baron et al.).

The application of the various kinds of interferon such as interferon-α, interferon-β and interferon-γ as the anticancer drug were tried by as many as 18 research groups, under the guidance of the Ministry of Health and Welfare "the Special Research regarding the Clinical application of Interferon" from the latter half of the 1970's even in Japan.

About these results, according to the report of Ohno ("Gan To Kagakuryoho", vol. 14, No. 5, pp. 1194–1202, 1987), the efficacy to the renal cell cancer is 6–23% with interferon-α and 4–20% with interferon-β; to the brain tumor in systemic administration is 4–20% with interferon-α and 13–17% with interferon-β; to the multiple myeloma is 0–30% with interferon-α and 4–25% with interferon-β; to the skin cancer in local administration is 48–72% with interferon-α and 33–53% with interferon-β. The approval of the application of these drugs has been obtained on the basis of these results. Additionally, interferon is also effective to hematopoietic tumors. Especially, interferon-α is effective to chronic lymphocytic leukemia in 3 cases of 19 cases; is effective to chronic myeloid leukemia in 4 cases of 14 cases; and is effective to hairy cell leukemia in 2 cases of 3 cases.

Unlike these results, the efficacy which is 0–6% to the solid tumor such as mammary carcinoma, stomach cancer and hepatocellular carcinoma has been hardly admitted.

Since interferon is certainly effective to renal cell cancer and hairy cell leukemia, which are not sensitive to the other anticancer drugs and exhibits some effects on multiple myeloma and malignant lymphoma on which the other drugs are ineffective, the efficacy of interferon is admitted. However, the results are still not satisfactory, since the interferon have almost no efficacy on solid tumors and the efficacy thereof is still around 20%, except the local administration of the drugs to skin cancer.

Efficacy of the interferon as therapeutic drugs for hepatitis B and hepatitis C is also approved based on antiviral actions thereof, as well as the applications based on antitumor effect thereof. It is known that hepatitis C causes chronic hepatitis and progress to liver cirrhosis, hepatocellular carcinoma in succession. It has been clarified that 80 percent of hepatocellular carcinoma occurs based on chronic hepatic diseases caused by the hepatitis C virus. The interferon has anti-viral activities to these hepatitis C viruses and allow the patients to be free from the virus and allow transaminase to be normal, and have become the first choice of therapy of hepatitis C (Ikegami et al., "Igaku No Ayumi", vol. 181, No. 5, pp. 341–344, 1997).

However, recent reports show that the effects of interferon are greatly affected by the amount of hepatitis C virus, that is, efficacy cannot be significantly obtained in hepatitis C patients with a large amount of the virus. Accordingly, how to improve the efficacy for these patients therefore becomes a big subject (Yatsuhashi et al., "Igaku No Ayumi", vol. 181, No. 5, pp. 333–336, 1997).

Okushin et al. indicated the possibility of a new approach to these problems ("Kanzo", vol. 36, pp. 735, 1995: and "Kanzo", vol. 38, No. 1, 1997). Specifically, they found that therapeutic results for hepatitis C patients that are not effective for conventional therapies can be markedly improved when an interferon-β is administered to such hepatitis C patients twice a day while a daily dose is divided into two doses per day.

The twice-a-day administration increases the effects to the virus replication, and additionally, increases antitumor activities, as reported by Tanahashi et al. ("Gan To Kagakuryoho", vol. 14, No. 4, pp. 1156–1159, 1987) and Niijima et al. (Cancer Immunology, Immunotherapy, vol. 30, No. 2, pp. 81–85, 1989). Namely, they administered a genetically recombinant human interferon-β to the urinary bladder cavity of patients with superficial bladder tumor at a dose of $3600 \times 10^4$ once a day or at a dose of $1800 \times 10^4$ twice a day, and evaluated the antitumor effects of the administration. Consequently, a higher efficacy can be obtained in the administration at a dose of $1800 \times 10^4$ twice a day than in the administration at a dose of $3600 \times 10^4$ once a day.

As described above, the reports on antiviral action or antitumor action show that the efficacy becomes higher in the administration of an interferon twice a day than in the administration in the same amount once a day. Although the mechanisms of antiviral and anti-tumor action of interferon have not been clarified yet, it is speculated that the antiviral action and anti-tumor action act under different mechanisms from each other, (Gewert et al., "Interferon", pp. 289–297, edited by Baron et al.; Fleischmann et al., "Interferon", pp. 299–309, 1992, edited by Baron et al.).

Since the effects on the anti-tumor activity have been obtained at a very high dose of $1800 \times 10^4$ units per dose per day and have been obtained with local administration, the effects with systemic administration such as intravenous administration have not been clarified yet. In particular, it is known that such interferon rapidly disappears from the blood circulation when they are intravenously administered (Satoh et al., "J. Interferon Res", vol. 4, No. 3, pp. 411–422, 1984).

As mentioned above, since the sufficient therapy or drug therapy have not been established yet in treatment of disease based on the abnormal proliferation of the cell, especially cancer, the establishment of the novel therapy and also drug therapy are hoped from now on.

Accordingly, an object of the present invention is to provide an industrially and medically useful novel method for inhibiting cell growth, which is directed to the therapy of cancers and of diseases occurred under a similar action mechanism, on which the interferon have not yet exhibited sufficient therapeutic effects.

DISCLOSURE OF INVENTION

The present invention provides a method for inhibiting cell growth, which includes the step of systemically administering a pharmaceutical preparation containing an interferon as an active ingredient two or more times a day.

BEST MODE FOR CARRYING OUT THE INVENTION

Figure 1:
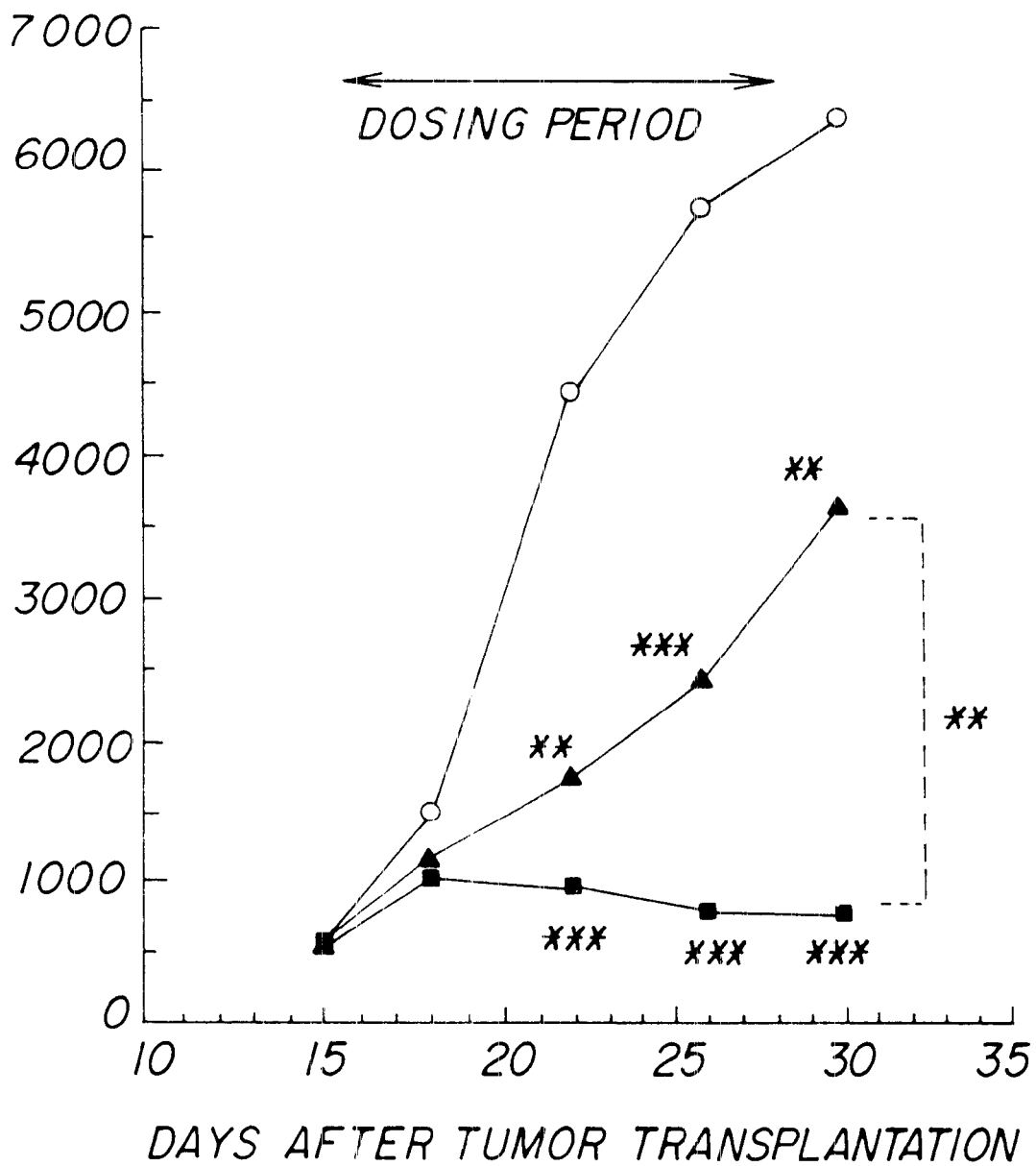
FIG. 1 is a graph showing differences in growth inhibitory effect on brain tumor among different medication methods of an interferon.

Interferon for use in the present invention may be any of interferon-α, -β, and -γ, and interferon of consensus type and hybrid type and may be derived from any of natural interferon, genetically recombinant interferon and chemically synthesized interferon. A genetically recombinant interferon-β and natural interferon-β are preferably used, of which a natural interferon-β is most preferable.

In the preparation of such interferon using the genetic recombination technologies, host cells include, for example, CHO (Chinese hamster ovary) cells, mouse C127 cells, and other mammalian cells: cells of insects such as silk worm and armyworms (*Mamestra brassicae*); and microorganisms such as *Escherichia coli, Bacillus subtilis,* and yeasts. Additionally, mice, rats, hamsters, rabbits, goats, sheep, pigs and cattle, for example, can also be used.

The interferon thus prepared can be purified and isolated from a conditioned medium if a cell culture, insect extract, microbial extract, and organism extract by a variety of chromatographic techniques. Such chromatography for use herein is not specifically limited as far as it has affinity to the interferon and includes, for example, a silicon dioxide (silica) or calcium phosphate column, metal chelate column, ion exchange column, and gel filtration column.

Separately, a natural interferon-β is generally prepared, for example, in the following manner. Interferon-β producing cells are cultured on the surface of, for example, a glass or plastic or on the surface of a microcarrier made of DEAE-dextran and are then subjected to induction treatment with, for example, a synthetic double-strand RNA such as Poly I:C and sequentially to super induction treatment (e.g., metabolic inhibition process by the combination use of cycloheximide and actinomycin D, or ultraviolet irradiation process), and the resulting cells are cultured in a culture medium for 20 to 48 hours, and an interferon-β is produced and is obtained as a culture medium containing interferon-β.

The interferon-β in the culture medium thus obtained is generally low in concentration, and the culture medium contains a variety of contaminants derived from cells or additives. The interferon-β must be concentrated and purified for medicaluse. A technique for the concentration and purification of interferon-β is not specifically limited, but is preferably a chromatographic technique using an insoluble carrier bonded with a blue dye and a metal-chelate-bonded carrier. Specifically, in the technique, a crude interferon-β-containing mixture is brought into contact with the insoluble carrier bonded with a blue dye, and the interferon-β is recovered as a solution using an eluant, and the interferon-β solution is brought into contact with the metal-chelate-bonded carrier in which a metal such as zinc is chelated, and the interferon-β is recovered using an eluant to thereby yield a concentrated and purified interferon-β.

The interferon for use in the present invention can be administered, as it is or as a pharmaceutical composition containing a carrier and excipient which are pharmaceutically allowable.

Formulation for administration can be prepared by a known method. For example, the interferon is generally dissolved in a sterile aqueous solution for use in injections, or is suspended in an extract, or is further emulsified to be embedded in liposome. A solid preparation can be prepared by a known method, for example, by a method in which an excipient such as mannitol, trehalose, sorbitol, lactose, glucose or raffinose is added to the interferon, and the resulting mixture is freeze-dried to yield a lyphilized preparation. Further, this lyophilized preparation can be powdered and is used as a powder. The resulting powder can be used as a solid by mixing the powder with, for example, polylactic acid or glycolic acid. A gel (gelatinized preparation) can be prepared by a known method such as a method in which the interferon is dissolved in a thickener or polysaccharide. Such thickeners include, for example, glycerol, polyethylene glycol, methylcellulose, carboxymethylcellulose, hyaluronic acid, and chondroitin sulfate.

Each of these pharmaceutical preparations may further comprise a stabilizer such as human serum albumin, human immunoglobulin α2-macroglobulin, and an amino acid; and a dispersing agent or absorbefacient such as an alcohol, sugar alcohol, ionic surfactant and nonionic surfactant, within a range not deteriorating the bioactivities of interferon. Additionally, the pharmaceutical preparations may further comprise a trace metal or an organic acid salt, if necessary.

The purified interferon-β preparation thus obtained is formulated into the aforementioned dosage form and can be used as a therapeutic agent which is useful in therapeutic treatment or prophylactic treatment of diseases due to abnormal cell growth and for which therapy and drug therapies have not yet been established, especially in diseases in which the target cell is a tumor cell of, for example, brain tumor or colon carcinoma.

A feature of the invented method is that a pharmaceutical preparation containing the interferon as an active ingredient is systemically administered two or more times a day for the inhibition of cell proliferation. Administration may be any of, for example, intravenous administration, intramuscular administration and subcutaneous administration, of which intravenous administration is preferably employed. As an administration schedule, the pharmaceutical preparation can be administered any times a day as far as it is administered two or more times a day, but is preferably administered twice a day. As an administration interval, the pharmaceutical preparation can be administered continuously two or more times a day or at intervals of nearly 24 hours (0 hr<administration interval<24 hr), but is preferably administered at intervals of from 1 hr to 23 hr.

A dose can be appropriately determined depending on, for example, the age and body weight of the patient, the condition of the patient, administration form, and administration route, and is generally in a range from $1 \times 10^4$ to $10000 \times 10^4$ units per dose per day, and preferably in a range from $10 \times 10^4$ to $1700 \times 10^4$ units per dose per day.

The present invention will be illustrated in further detail with reference to several examples below, which are not intended to limit the scope of the invention.

EXAMPLES

Example 1 and Comparative Example 1

A tumor block of human brain tumor U 251-SP was subcutaneously transplanted to nude mice (Balb/c nu/nu). After confirming the growth (proliferation) of the tumor (16 days after transplantation), a placebo and a natural human interferon-β ("Feron" available from Toray Industries, Inc.) were administered to the mice every day. In a control group, the placebo was administered to the mice via tail vein twice a day in the morning and evening. The interferon-β was administered at a dose of $100 \times 10^4$ international units per individual once a day, and at a dose of $50 \times 10^4$ international units per individual twice a day in the morning and evening. In the once-a-day administered group at a dose of $100 \times 10^4$ international units per individual, the interferon-β was administered in the morning and the placebo was administered in the evening.

The size of tumor was determined over time using micrometer calipers, and the volume of tumor (mm³) was calculated according to the following equation: Tumor volume (mm³)=Major axis (mm)×Minor axis (mm)²/2 (as mean among eight mice per group).

FIG. 1 is showing the difference in the growth inhibitory effect by the difference of the administration protocol of interferon. The ordinate shows the tumor volume that was calculated from tumor diameter and the abscissa indicates the number of the days after tumor implantation The tumor growth in the once-a-day administered group (closed triangle) at a dosage of $100 \times 10^4$ international units interferon-β of per head was significantly suppressed about 50% to 60% of that in the control group (open circle) at 30 days after tumor implantation. In contrast, the tumor growth in the twice-a-day administered group (closed square) at a dosage of $50 \times 10^4$ international units of interferon-β per head was more significantly suppressed about 15% to 25% compared to that in the once-a-day administered group at a dosage of $100 \times 10^4$ international units interferon-β per head, even through the total doses per day were equal in the two groups, and about 10% to 15% compared to that in the control group. (*: p<0.05, : P<0.01, *: p<0.001, versus the control group).

Example 2 and Comparative Example 2

A tumor block of human colon carcinoma LS 180 was implanted to nude mice subcutaneously (Balb/c nu/nu). After confirming the growth (proliferation) of the tumor (15 days after inoculation), placebo and natural human interferon-β ("Feron" available from Toray Industries, Inc.) were administered to the mice every day. In a control group, the placebo was administered to the mice via tail vein twice a day in the morning and evening. The interferon-β was administered at a dosage of $100 \times 10^4$ international units per head once a day, and at a dosage of $50 \times 10^4$ international units per individual twice a day in the morning and evening. In the once-a-day administered group at a dosage of $100 \times 10^4$ international units per head, the interferon-β was administered in the morning and the placebo was administered in the evening.

The size of tumor was determined sequentially using micrometer calipers, and the volume of tumor (mm³) was calculated according to the following equation: Tumor volume (mm³)=[Major axis (mm)]×[Minor axis (mm)]²/ 2 (as mean among five mice per group).

Figure 2:
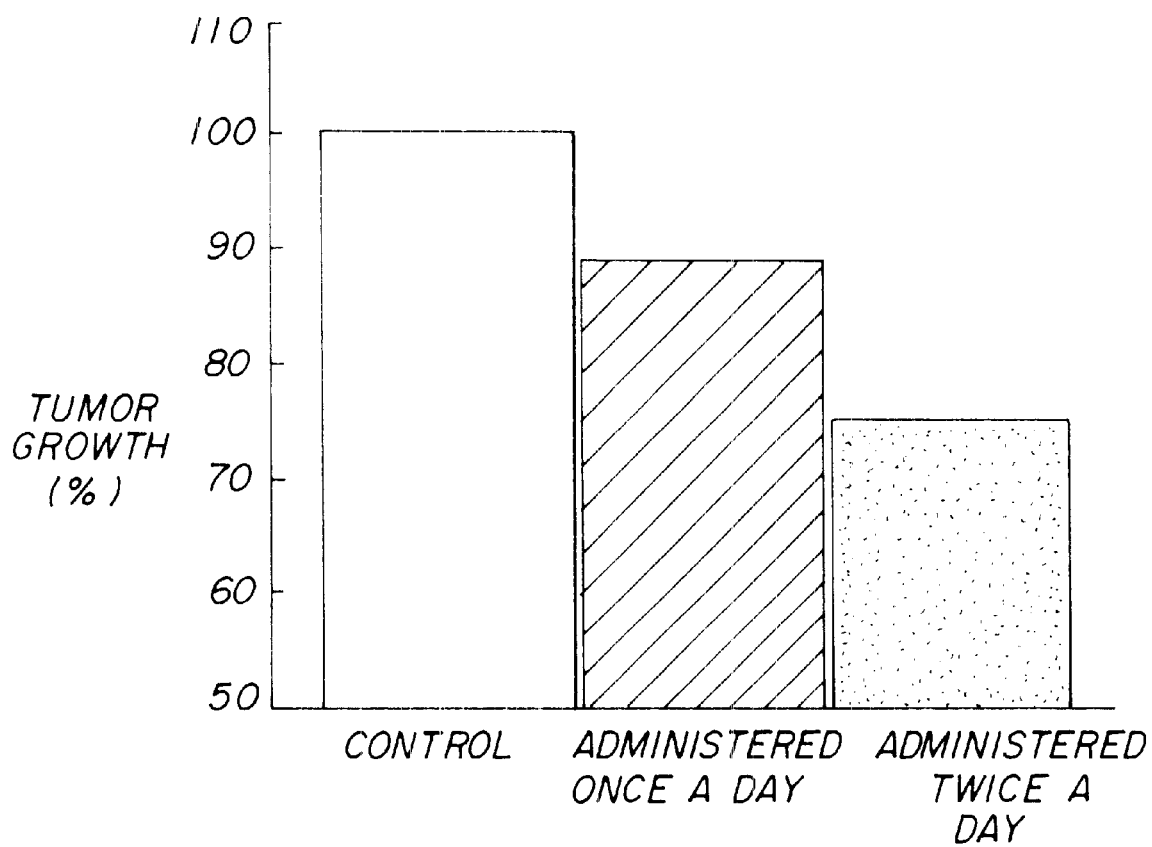
FIG. 2 is a graph showing differences in growth inhibitory effect on colon carcinoma among different medication methods of an interferon.

FIG. 2 is showing the difference of the growth inhibitory effect by the difference of the administration protocol of interferon with the proliferation rate at 30 days after tumor inoculation. The tumor volume in the once-a-day administered group (hatched column) at a dosage of $100 \times 10^4$ international units interferon-β per mouse was suppressed about 10% compared to that in the control group (open column). In contrast, the tumor volume in the twice-a-day administered group (closed column) at a dosage of $50 \times 10^4$ international units of interferon-β per mouse was suppressed about 15% compared to that in the once-a-day administered group at a dosage of $100 \times 10^4$ international units interferon-β per mouse, even through the total dosages per day were equal in the two groups, and about 25% compared to that in the control group.

INDUSTRIAL APPLICABILITY

The invented method can improve the anti-tumor effects remarkably and can provide effective means to cancer treatment.

What is claimed is:

1. A method for inhibiting brain tumor or colon carcinoma cell growth comprising systemically administering a pharmaceutical preparation including an interferon-β as an active ingredient two or more times a day.

2. A method for inhibiting brain tumor or colon carcinoma cell growth according to claim 1, wherein said interferon is a natural interferon.

3. A method for inhibiting brain tumor or colon carcinoma cell growth according to claim 1, wherein the interferon is administered at a dosage range from $10 \times 10^4$ to $1700 \times 10^4$ units per administration.

* * * * *